United States Patent [19]
Quintero et al.

[11] Patent Number: 6,027,530
[45] Date of Patent: Feb. 22, 2000

[54] SYSTEM, APPARATUS AND METHOD FOR CHEMICAL FIXATION OF STENTLESS CARDIAC VALVULAR BIOPROSTHESES

[75] Inventors: Lillian Quintero, Garden Grove; Diana Nguyen-Thien-Nhon, Santa Ana, both of Calif.

[73] Assignee: Baxter International Inc., Deerfield, Ill.

[21] Appl. No.: 08/997,766

[22] Filed: Dec. 24, 1997

[51] Int. Cl.[7] .................................................. A61F 2/24
[52] U.S. Cl. ............................... 623/2; 623/901; 8/94.11
[58] Field of Search ................................. 623/2, 12, 901; 600/36; 8/94.11

[56] References Cited

U.S. PATENT DOCUMENTS

| | | |
|---|---|---|
| 3,409,013 | 11/1968 | Berry . |
| 3,548,418 | 12/1970 | Angell et al. . |
| 4,056,854 | 11/1977 | Boretos et al. . |
| 4,182,446 | 1/1980 | Penny . |
| 4,185,636 | 1/1980 | Gabbay et al. . |
| 4,372,743 | 2/1983 | Lane . |
| 4,702,250 | 10/1987 | Ovil et al. . |
| 4,865,600 | 9/1989 | Carpentier et al. . |
| 5,041,131 | 8/1991 | Nagase . |
| 5,089,015 | 2/1992 | Ross . |
| 5,197,979 | 3/1993 | Quintero et al. . |
| 5,279,612 | 1/1994 | Eberhardt ..................... 623/2 |
| 5,449,384 | 9/1995 | Johnson ....................... 623/2 |
| 5,769,780 | 6/1998 | Hata et al. ................... 623/901 |

FOREIGN PATENT DOCUMENTS

| | | |
|---|---|---|
| 0 073 624 | 3/1982 | European Pat. Off. . |
| 0 165 622 | 12/1985 | European Pat. Off. . |
| 0 402 036 | 12/1990 | European Pat. Off. . |
| 1167328 | 5/1987 | Italy . |
| 2 108 393 | 5/1983 | United Kingdom . |
| 8401894 | 5/1984 | WIPO ...................... 623/2 |
| WO 95/14443 | 6/1995 | WIPO . |
| WO 96/40012 | 12/1996 | WIPO . |

OTHER PUBLICATIONS

D. F. Del Rizzo, et al., "Initial Clinical Experience with the Toronto Stentless Procine Valve™", Journal of Cardiac Surgery, vol. 9, 379–385, 1994.

M. Höfig, et al., "Surgery for Acquired Heart Disease: Performance of a Stentless Xenograft Aortic Bioprosthesis up to Four Years After Implantation", The Journal of Thoracic and Cardiovascular Surgery, vol. 103, No. 6, 1068–1073, Jun. 1992.

T. E. David, et al., "Aortic Valve Replacement with a Stentless Porcine Aortic Valve: A Six–year Experience", The Journal of Thoracic and Cardiovascular Surgery, vol. 108, No. 6, 1030–1036, Dec. 1994.

T. E. David, et al., "Aortic Valve Replacement with Stentless Porcine Bioprostheses", Journal of Cardiac Surgery, vol. 3, No. 4, 501–505, Dec. 1988.

T. E. David, et al., "Aortic Valve Replacement with Stentless Porcine Aortic Bioprosthesis", The Journal of Thoracic and Cardiovascular Surgery, vol. 99, No. 1, 113–118, Jan. 1990.

(List continued on next page.)

*Primary Examiner*—Bruce E. Snow
*Attorney, Agent, or Firm*—Robert D. Buyan; Guy L. Cumberbatch

[57] ABSTRACT

A system, apparatus and method for tanning of a stentless aortic bioprosthesis, and articles manufactured by such method. The system includes a circulating bath which contains a tanning solution, and a support insert apparatus upon which the bioprosthesis is mounted during the tanning prosthesis. The support insert has i) two (2) coronary Sinus of Valsalva support projections for maintaining the coronary Sinuses of Valsalva in their substantially open, non-collapsed configurations, and ii) one (1) non-coronary Sinus of Valsalva support projection for maintaining the non-coronary Sinus of Valsalva in its substantially open, non-collapsed configuration, during tanning. Additionally, the system may include internal or external support members for maintaining the patency of right and left coronary artery segments, such coronary artery segments being permitted to remain attached to the Aortic bioprosthesis during tanning.

22 Claims, 3 Drawing Sheets

OTHER PUBLICATIONS

Medtronic, Inc. Brochure for the "Freestyle® Aortic Root Bioprosthesis Implant", 1995.

St. Jude Medical, Inc. Brochure for "The Toronto SPV™ Stentless Bioprosthesis", 1993.

Baxter Edwards AG, Edwards CVS Division Brochure "Edwards Prima™ Stentless Bioprosthesis", 1995.

Baxter Edwards AG, Edwards CVS Division Brochure "Edwards Prima™ Stentless Bioprosthesis Modified Model 2500", 1996.

SYSTEM, APPARATUS AND METHOD FOR CHEMICAL FIXATION OF STENTLESS CARDIAC VALVULAR BIOPROSTHESES

FIELD OF THE INVENTION

The present invention relates generally to methods of manufacturing implantable medical devices formed of preserved animal tissue, and more particularly to a system, apparatus and method for chemical fixation (i.e., "tanning") stentless aortic bioprostheses which have been harvested from mammalian donors.

BACKGROUND OF THE INVENTION

Heart valves harvested from animals, such as porcine heart valves, have proven to be useable as bioprosthetic replacements for malfunctioning endogenous heart valve. These animal heart valves typically contain large amounts of connective tissue proteins, such as collagen and elastin. After the heart valve and/or other desired tissues have been harvested from the donor animals, they undergo a chemical "tanning" process wherein the connective tissue proteins within the tissue are exposed to one or more chemical cross linking agents (i.e., "fixatives" or "tanning agents") These crosslinking agents then react with the connective tissue proteins to form chemical cross linkages between (or sometimes within) the connective tissue protein molecules. The types of chemical cross linking agents useable for the tanning process include: formaldehyde, glutaraldehyde, dialdehyde starch, hexamethylene diisocyanate and certain polyepoxy compounds. The tanning process renders the animal tissue relatively inert with respect to the living host environment, and brings about fixation (i.e., stabilization) of the tissue so that it has a fixed configuration and does not degrade following implantation.

One particular type of bioprosthetic heart valve which has gained popularity among surgeons in recent years, is known as a "stentless aortic bioprosthesis." Such stentless aortic bioprostheses do not include any man-made stent or support frame, and are formed entirely of a preserved segment of the donor animal's aorta, having the aortic valve leaflets therein.

Examples of commercially available stentless bioprosthetic valves include the Edwards Prima™ Stentless Bioprosthesis (Baxter Edwards AG, Spierstrasse 5, CH-6848 Horw, Switzerland), the Medtronic Freestyle™ Aortic Root Bioprosthesis (Medtronic, Inc. 7000 Central Avenue NE, Minneapolis, Minn. 55432-3576) and the St. Jude Toronto™ SPV Stentless Bioprosthesis (St. Jude Medical, Inc. One Lillehei Plaza, St. Paul, Minn. 55117).

The tanning of stentless bioprosthetic heart valves presents unique technical challenges because, due to the absence of any stent or man made support structure, it is necessary to temporarily support the stentless bioprosthesis during its exposure to the tanning agent(s). A particular system and method for tanning of stentless bioprostheses has been described in U.S. Pat. No. 4,372,743 (Lane) entitled "Low-Pressure Fixation of Valvular Tissue Intended for Implantation." However certain components of this system are less than optimal for the tanning of some types of aortic bioprostheses. In particular, the fixation apparatus disclosed in U.S. Pat. No. 4,372,743 (Lane) does not fully support the Sinuses of Valsalva, located within the aortic portion of the bioprosthesis, and thus some deformation or collapse of these sinuses may occur during the tanning process.

Thus, there exists a need in the art for the development of a new system, apparatus and method for tanning of stentless aortic bioprostheses such that the Sinuses of Valsalva will be fixed in substantially open, non-collapsed configurations.

SUMMARY OF THE INVENTION

The present invention provides a system and method for tanning of an aortic bioprosthesis while supporting the coronary and non-coronary Sinuses of Valsalva to prevent deformation or collapse of these sinuses during the tanning process. Also, the system of the present invention may incorporate apparatus to maintain the patency of segments of the donor animal's coronary arteries which may be permitted to remain attached to the bioprosthesis in accordance with a new type of stentless aortic bioprosthesis as described in copending U.S. patent application Ser. No. 08/998,318 filed Dec. 24, 1997 entitled "Stentless Bioprosthetic Heart Valve With Coronary Protuberances and Related Methods for Surgical Repair of Defective Heart Valves," which is hereby expressly incorporated by reference. This new stentless bioprosthesis includes preserved, patent, useable segments of the donor animal's coronary arteries which extend outwardly from the aortic portion of the bioprosthesis which has segments of the donor animal's coronary arteries remaining attached thereto. Alternatively, the tanning system of the present invention may also be used for tanning of other types of stentless aortic bioprostheses which may be devoid of such coronary artery segments.

Further in accordance with the invention, there is provided an aortic bioprosthesis tanning system which incorporates a support insert configured to hold and support the stentless aortic bioprosthesis during the tanning process. This support insert is specifically configured to maintain the natural anatomical configuration of the three (3) Sinuses of Valsalva (i.e., a left coronary sinus, a right coronary sinus, and a non-coronary sinus) during the tanning process. In this regard the support insert has two (2) generally convex coronary sinus support members, and one (1) generally convex non-coronary sinus support member, formed thereon. Such maintenance of the Sinuses of Valsalva in their substantially open, non-collapsed configurations during the tanning process is particularly important when tanning aortic bioprostheses which have patent coronary artery segments attached thereto, such as that described in copending U.S. patent application Ser. No. 08/998,318. Thus, to further facilitate the tanning of such bioprostheses having patent coronary artery segments, the tanning system of the present invention may additionally include coronary segment lumen supports (e.g., mandrels or other internal or external support member(s)) to maintain the patency of the coronary artery segments during tanning.

Further in accordance with the invention, there is provided a method for tanning a stentless aortic bioprosthesis by mounting the bioprosthesis on an insert of the foregoing character during the tanning process. In instances where the bioprosthesis has segments of the donor animal's coronary arteries remaining attached thereto, the method may further comprise the step of utilizing internal and/or external supports to maintain the openness and patency of the coronary segment lumens during the tanning process.

Still further in accordance with the present invention, there are provided stentless aortic bioprostheses which have been manufactured (i.e., tanned) using the tanning system and/or support insert/members of the foregoing character.

Further objects and advantages of the present invention will be apparent to those skilled in the art from the following particular description.

DESCRIPTION OF THE PREFERRED EMBODIMENTS

Throughout this description, the preferred embodiment and examples shown should be considered as exemplars, rather than limitations on the apparatus and methods of the present invention.

Although exemplary embodiments of the present invention have been shown and described, it will be apparent to those having ordinary skill in the art that a number of changes, modifications, or alterations to the invention as described herein may be made, none of which depart from the spirit of the present invention. All such changes, modifications and alterations should therefore be seen as within the scope of the present invention.

Figure 1:
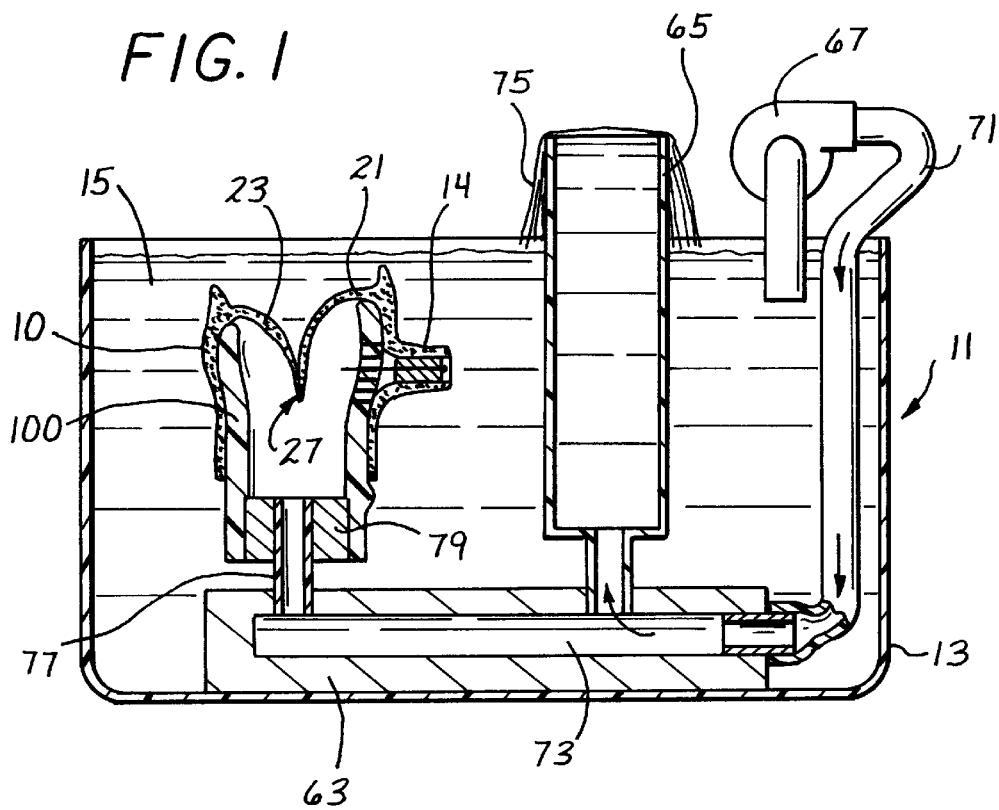
FIG. 1 is a sectional view of a preferred chemical tanning system useable to tan a stentless aortic bioprosthesis of the present invention, such bioprosthesis being mounted upon a support insert of the present invention.

FIG. 1 shows a chemical fixation system 11 which is useable for low pressure fixation (i.e., "tanning") of a porcine aortic bioprosthesis 10. The system 11 generally comprises a tank 13 filled with tanning solution 15, and an insert 100 upon which the stentless aortic bioprosthesis 10 is mounted.

As shown in FIGS. 2, 2a, 4 and 5, the particular aortic bioprosthesis 10 is formed of a preserved segment of mammalian aorta 12 having an inflow rim or inflow end IE, an outflow rim or outflow end OE, and the donor animal's aortic valve leaflets 20 positioned therewithin. Segments of the donor animal's right and left main coronary arteries 14a, 14b extend from the aortic segment 12, and such coronary artery segments 14a, 14b have open, patent lumens 15a, 15b which extend therethrough. This bioprosthesis 10 is preferably of porcine origin.

After the bioprosthesis has been harvested from the donor animal, the coronary artery segments 14a, 14b are trimmed to a desired length. The length of these coronary segments is typically 1–6 mm and preferably as long as possible (i.e., up to the first coronary bifurcation present on each main coronary artery of the donor animal. After the coronary segments 14a, 14b have been trimmed, mandrel members 16 are inserted into the lumens 15a, 15b of the coronary segments 14a, 14b to maintain the patency of those lumens 15a, 15b during the tanning process. Ligatures 18 are tied about the coronary segments 14a, 14b to hold the mandrel members 16 in the lumens 15a,15b during the tanning process.

After the bioprosthesis 10 has been trimmed and the mandrel members 16 have been inserted into and secured within the coronary segment lumens 15a, 15b, the bioprosthesis is mounted upon an insert 100. This insert supports and maintains the desired configuration of the bioprosthesis 10 during the tanning process. The preferred insert 100, as specifically shown in FIGS. 2, 3a and 3b, comprises a generally tubular member having a top end TE, a bottom end BE, an outer surface 102, an inner surface 104, and a hollow bore 106 extending longitudinally therethrough.

At the top end TE of the insert 100, there are formed two (2) coronary Sinus of Valsalva supports 110a, 110b and one (1) non-coronary Sinus of Valsalva support 112. The coronary Sinus of Valsalva supports 110a, 110b have outer surfaces 114a, 1 14b which are of convex or outwardly curved configuration which is substantially the same as the substantially open shape of the right and left coronary Sinuses of Valsalva, located adjacent the right and left coronary ostia within the harvested bioprosthesis 10. A plurality of through holes 118 are formed in each of the coronary Sinus of Valsalva supports 114a, 114b, as shown.

The non-coronary Sinus of Valsalva support 112 also has an outer surface 116 which is of convex or outwardly curved configuration, but less so than the outer surfaces 114a, 114b of the two (2) coronary Sinus of Valsalva supports 110a, 110b. The non-coronary Sinus of Valsalva support 112 is shorter than the coronary Sinus of Valsalva supports 110a, 110b, and its outer surface 116 is substantially the same as the shape of the inner wall of the non-coronary sinus (i.e., region of the interior of the ascending aorta, opposite and midway between the right and left coronary Sinuses of Valsalva) of the donor animal's aorta. Generally U-shaped recesses 47 are formed between the supports 110a, 110b, and 112. Thus, these configurational aspects of the upper portion UP of the insert 100 are analogues to the shape of the interior of the donor animal's aortic root, when its Sinuses of Valsalva are substantially in their dilated or open configurations.

The lower portion LP of the insert 100 has a wall of generally cylindrical configuration which is open at both ends and which defines the central bore 106 of the insert 100. An annular step 108 is formed about the inner surface 104 of the hollow bore 106, at a spaced distance from the bottom end BE, as shown in FIG. 2.

Figure 2:
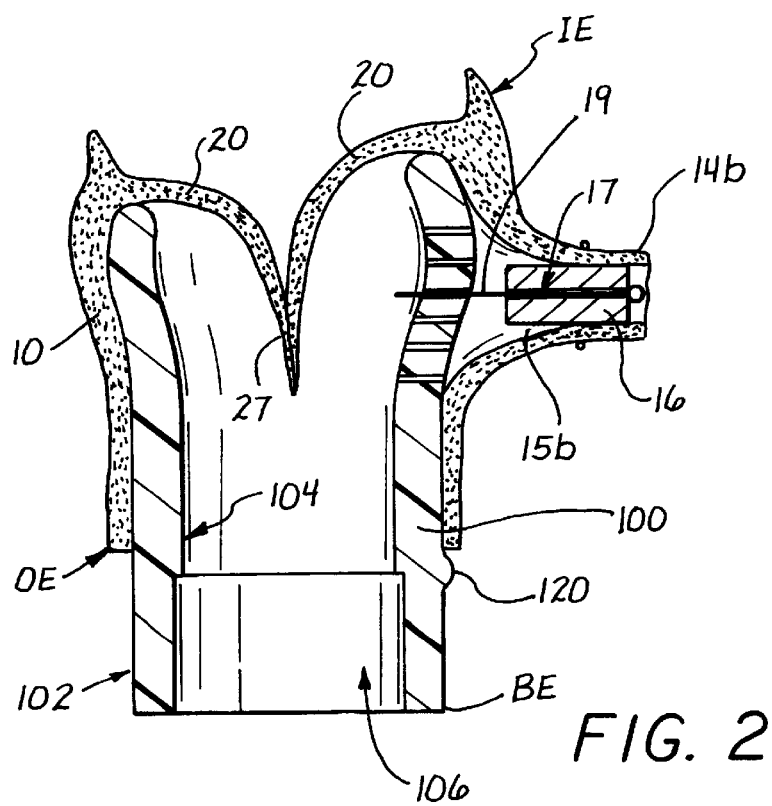
FIG. 2 is a longitudinal sectional view through the bioprosthesis and support insert shown in FIG. 1.
Figure 2A:
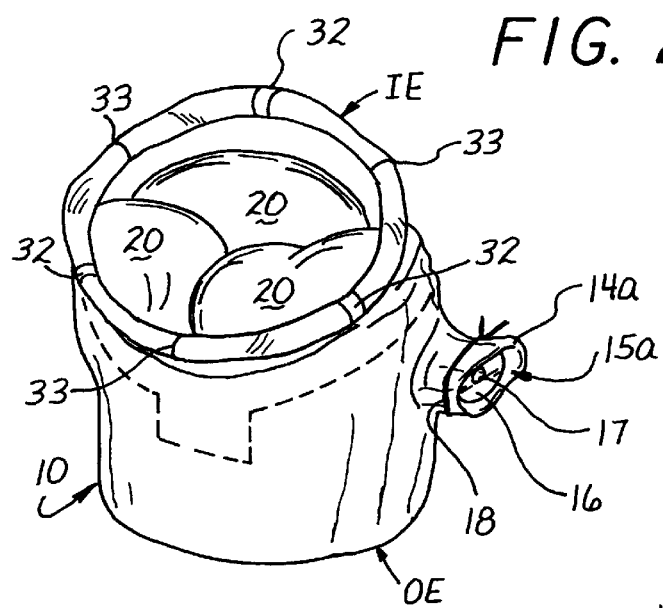
FIG. 2a is a perspective view of a stentless aortic bioprosthesis of the present invention.

As shown in FIG. 2, the bioprosthesis 10 with the mandrel members 16 inserted within its coronary segments 14a, 14b, is mounted on the insert 100 such that the top end TE of the insert 100 is within the main lumen of the bioprosthesis, the coronary supports 110a, 110b are positioned within the right and left coronary Sinuses of Valsalva respectively, and the non-coronary support 112 is positioned within the non-coronary Sinus of Valsalva. The aortic portion 12 of the bioprosthesis 10 extends downwardly over the outer surface 102 of the insert 100, and the outflow end OE of the bioprosthesis is located immediately above a marker bump 120 which is formed on and extends outwardly from the outer surface 102 of the insert 100, as shown in FIG. 2.

In the particular example shown in the drawings, the mandrel members 16 have bores 17 which extend longitudinally therethrough. The bore 17 of each mandrel member 16 is alignable with one of the through holes 118 formed in the adjacent coronary support member 110a or 110b. A pin 19 is inserted through each mandrel member bore 17 and into a through hole 18 of the adjacently situated coronary support member 110a or 110b to secure the bioprosthesis 10 upon the insert 100 during the fixation process.

In the preferred embodiment shown in the drawings, the mandrel members 16 are formed of silicone tubing, but they may be formed of other materials such as polyurethane, polyester, polytetraflouroethylene (PTFE), polyethylene, stainless steel, titanium or a metal alloy. The insert 10 may be molded or machined from a biocompatible material which does not react chemically with the tanning solution 15. One particular material of which the insert 100 may be formed is epoxy resin, although various alternative materials may be used. The insert 100 is preferably sufficiently transparent to permit one to view the inner wall of the bioprosthesis 10 while it is mounted on the insert 100.

When the bioprosthesis 10 is properly mounted on the insert 100, the recesses 47 will serve to prevent the insert 100 from coming into contact with, and causing damage to, the valve leaflets 20 at the commissures 27. To avoid damaging the tissue of the bioprosthesis 10, the tissue-contacting surfaces 102, 114a, 114b, 116 are smooth and devoid of potentially traumatic projections or burrs. Similarly, the outer edges of the supports 110a, 110b, 112 and the inner edges of the recesses 47 are smoothly curved and devoid of sharp corners.

The system 11 may be used to tan one or more bioprostheses 10 mounted upon inserts 100 in the manner described above. The system includes a tank 13, a header 63, a reservoir 65 coupled to the header 63, a pump 67, an intake conduit 69 leading from the tanning solution 15 within the tank to the intake of the pump, and a discharge conduit 71 leading from the discharge of the pump to the header 63. The header 63 is fixed within the tank 61 and has a passage 73 coupled to the conduit 71 and to the lower end of the reservoir 65. The tanning solution 15 fills the tank 61 to a predetermined height, and the reservoir 65 has an open top 75 which lies a prescribed distance above the elevation of the tanning solution 15 in the tank 61. The difference in elevation between the levels of the tanning solution 15 within the tank 61 and the reservoir 65 represents the differential pressure across the valve leaflets 21, 23 and 25 at which the tanning process will be carried out. This is a static head and flow is required only to make up for leakage, and a slight initial flow is required to close the valve leaflets 21, 23 and 25. In the embodiment illustrated, the head represented by the difference in these two elevations is 2 mm Hg.

The passage 73 in the header 63 also communicates with a riser 77 having a stopper 79 mounted thereon. The upper end of the stopper 79 is received within the lower end of the insert 17 until it abuts against the annular step 108, thereby ensuring that the stopper 79 and insert 100 will cooperate to mount the valve 13 vertically within the tank 61, as desired. Additional valves 13 may be similarly mounted on the header 63, if desired.

The tanning solution 15 may be of any composition capable of crosslinking connective tissue proteins (i.e., collagen and elastin) present in the tissue of the bioprosthesis 10.

With the components in the position of FIG. 1, the pump 67 can be operated to pump tanning solution 15 from the tank 61 through the conduits 69 and 71, the header 63 and over the top 75 of the reservoir 65 as may be required to maintain the desired static head. The flowrate of the fixative solution through the bioprosthesis is zero, or at least sufficiently low to avoid placing any velocity load on the leaflets 20. Thus, the interior of the bioprosthesis 10, including the interiors of the valve leaflets 20 is subjected to a static pressure increasing to the height of the top 75. Simultaneously, the outer surface of the bioprosthesis are subjected to the tanning solution 15 at a static pressure which corresponds to the elevation of the tanning solution in the tank 61. Preferably, the differential pressure to which the bioprosthesis 10 (and in particular the delicate valve leaflets 20) is subjected corresponds to the difference in elevation between the top 75 of the reservoir 65 and the level of the tanning solution 15 within the tank 61. This assures that the internal pressure within the bioprosthesis 10 will exceed the exterior pressure so that the valve leaflets 20 will be urged toward the closed position. Also, because the liquid level in the reservoir 65 cannot rise above the top 75, the maximum internal pressure is also regulated. By utilizing a known volume of the tanning solution 15 in containers of known volume, the differential pressure across the valve leaflets 20 can be maintained at the desired nominal value.

The action of the tanning solution 15 on the bioprosthesis 10 tends to shrink and distort the bioprosthesis 10. However, the engagement of the bioprosthesis 10 in the region of the Sinuses of Valsalva 31 against the relatively rigid coronary and non-coronary Sinus of Valsalva supports 110a, 110b and 112, prevents significant distortion of these critical portions of the bioprosthesis 10, and maintains the substantially open, normal anatomical configurations of the Sinuses of Valsalva during the tanning process. This is particularly important in the preferred bioprosthesis 10, in order to facilitate substantially natural, non-turbulent flow of blood from the main lumen of the bioprosthesis 10 into the coronary segment lumens 15a, 15b. The tissue adjacent the right coronary valve leaflet 20 contains additional muscle, and the conforming shape of the right Sinus of Valsalva support 110b engages the base of the right coronary leaflet 20 to prevent significant distortion and shrinkage in this highly muscular region. Also, the lower regions of the bioprosthesis 10 engage the outer surface 102 of the lower portion LP of the insert 10 so as to maintain the natural shape of the lower portion LP, without shrinkage or distortion.

The bioprosthesis 10 remains in contact with the tanning solution 15 for a sufficient time to obtain fixation of the bioprosthesis. The actual fixation time will be determined by the particular chemical fixative agent used, and the concentration thereof. The chemical fixative agents which are useable for this purpose include glutaraldehyde, formaldehyde, dialdehyde starch, hexamethylene diisocyanate and certain polyepoxy compound(s), as well as combinations of these agents. The presently preferred fixative agent is a solution of 0.625% buffered glutaraldehyde, and the preferred exposure time for the bioprosthesis in fixative system 11 containing this preferred fixative is 3–24 hours.

After the tanning process is complete, the bioprosthesis 10 is removed from the tanning solution and the internal or external support members (e.g., mandrel members 16) are removed. As specifically shown in FIG. 5, in applications wherein internal support members such as the mandrel members 16 have been secured by ligatures 18, such ligatures 18 will typically be removed prior to extraction of the mandrel members 16. Thereafter, if necessary, any distal portions 19 of coronary artery segments 14a, 14b of length $L_2$ located beneath or distal to the ligatures 18 may be cut away and discarded, so as to leave remaining coronary segments 14a, 14b of length $L_1$ and of substantially normal anatomical configuration attached to the bioprosthesis 10. In this regard, it is desirable that such ligatures 18 be placed as distal as possible, so as to maximize the length $L_1$ of the coronary artery segments 14a, 14b which remain after the distal portions of the coronary segments 14a, 14b have been cut away and discarded. Preferably, the length $L_1$ of the coronary artery segments remaining after final trimming will be at least 1–2 mm and typically in the range of 2–6 mm, while the length $L_2$ of the discarded distal coronary segments 19 is preferably less than 4 mm and typically about 1 mm.

After the internal or external support members (e.g., mandrels 16) have been removed and the coronary artery segments 14a, 14b have undergone final trimming (if necessary), the bioprosthesis 10 is then sterilized by a suitable sterilization technique, such as immersion in a biocompatible sterilization solution. The bioprosthesis is then measured to determine its outside diameter, and such outside diameter may be rounded off to the nearest millimeter.

After the bioprosthesis 10 has been sized, it is subjected to a second trimming step in which substantially all of the myocardial tissue is shaved away, leaving a thin cartilage rim adjacent to the right coronary septal shelf for reinforcement. The left and right coronary artery segments 14a, 14b are allowed to remain. All trimming is conducted with the goal leaving an intact aortic wall segment above the protruding coronary segments 14a, 14b, such intact aortic wall segment being of sufficient width to a) maintain proper alignment of the commissure, b) prevent distortion of the bioprosthesis 10 during suturing, and/or c) permit replacement of a supracoronary segment of the patient's ascending aorta (e.g., a "total root replacement") if so desired.

Finally, the inflow end IE of the bioprosthesis 10 is trimmed on the same plane as the cusps of the valve leaflets 20, usually leaving an intact segment of about 3 to 4 mm in width as measured from the hinge of the leaflet. All of the fatty tissue in the aorta is trimmed away.

Figure 3:
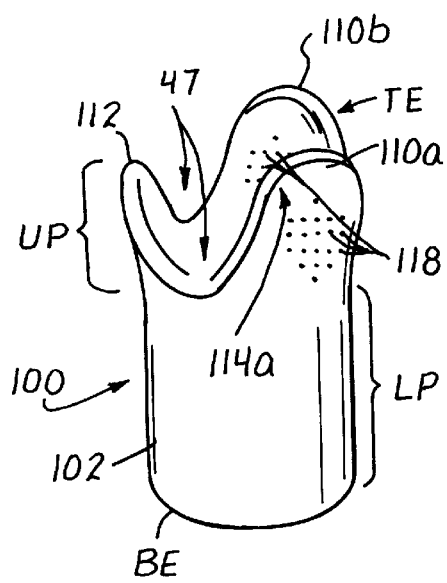
FIG. 3 is a perspective view of a preferred bioprosthesis support insert of the present invention.
Figure 3A:
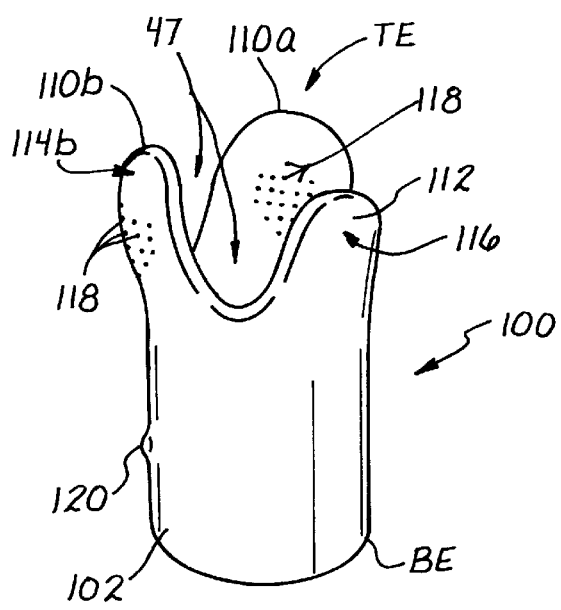
FIG. 3a is another perspective view of the bioprosthesis support insert of FIG. 3.
Figure 4:
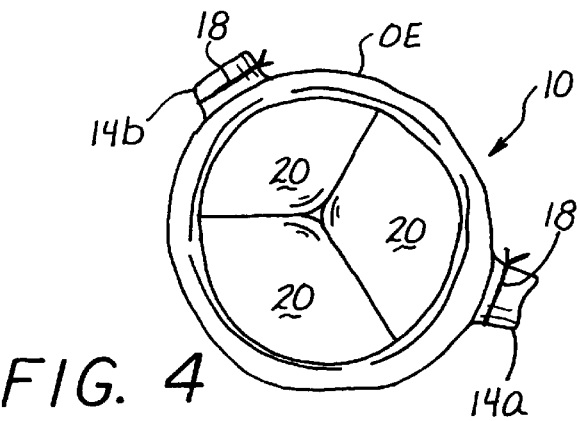
FIG. 4 is a plan view of the outflow end of the preferred stentless aortic bioprosthesis of the present invention.
Figure 5:
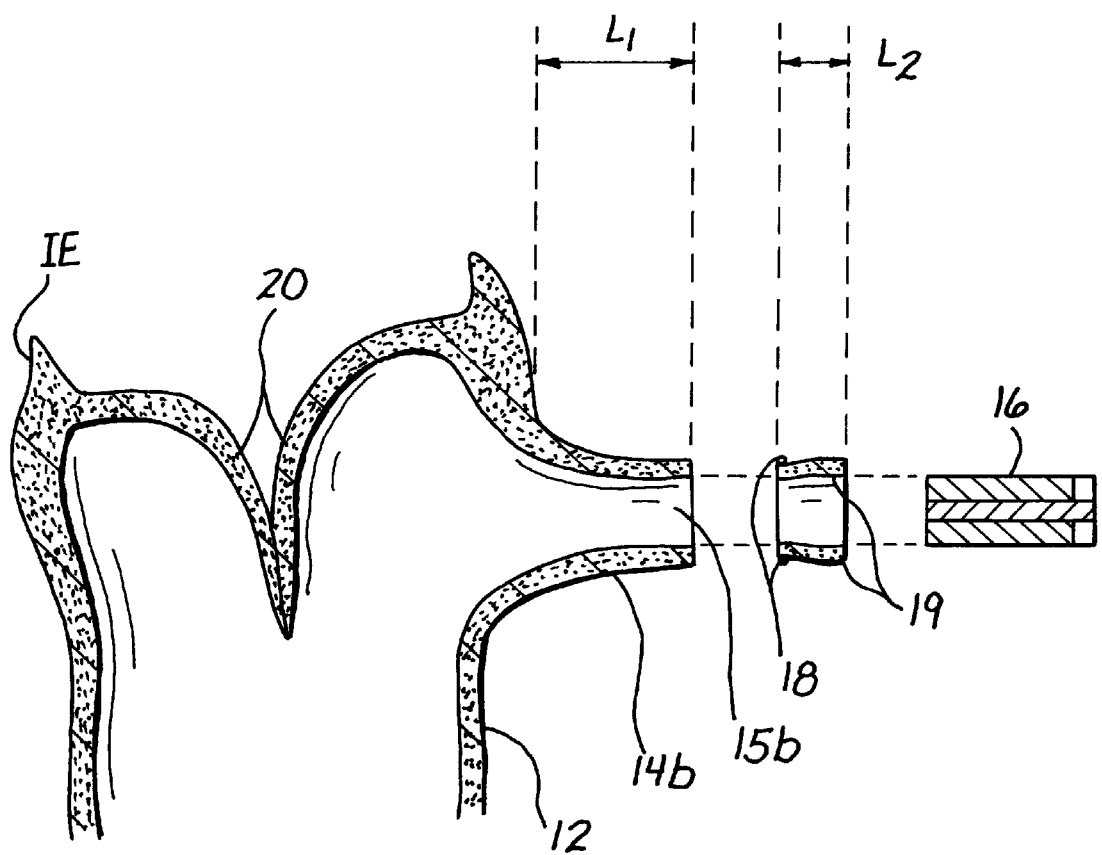
FIG. 5 is a partially exploded, longitudinal sectional view of the stentless aortic bioprosthesis of FIG. 2, showing the manner in which the coronary artery segments may be trimmed following the tanning of the bioprosthesis.

As shown in FIGS. 3a and 3b, the resulting aortic segment 12 contains three valve leaflets 20, each of which is affixed to the aortic segment 12 at a juncture. The inner edges 25 of the valve leaflets 20 meet when the leaflets 20 are in their closed positions, as shown in the drawings. Also, the leaflets 20 form commissures at their junctions with the aortic wall, and the leaflets are joined to the aortic segment 12 along a leaflet junctures 29. The wall of the aortic segment 12 adjacent junctures 29 forms the Sinuses of Valsalva. The leaflet 20 closest to the right coronary artery segment 14a, is positioned somewhat asymmetrically with respect to the other two leaflets 20.

A fabric covering (not shown) may optionally be disposed about the inflow end IE of the bioprosthesis 10 and/or upon a portion of one side of the bioprosthesis 10 which corresponds to the right coronary septal shelf. Such fabric covering enhances the strength of the inflow end IE of the bioprosthesis 10 which is sutured to the native aortic annulus, and thus serves to deter the sutures from tearing through the tissue of the bioprosthesis 10. As described in copending United States patent application Ser. No. (TBD) this fabric covering may be formed of a thin, biocompatible material which is strong enough to hold sutures. For example, such fabric covering may be formed of woven polyester having a thickness of 0.008 inch" and a weight of 72 grams per square meter. The fabric used for the covering is preferably cut on the diagonal to assure a snug fit around curved surfaces. The fabric is then sewn to the bioprosthesis 10 by hand or other appropriate means, using a nonabsorbable, biocompatible thread.

Mid-cusp markings 32, such as stitches formed of thread of a color which contrasts with the body of the bioprosthesis 10, may be formed on the above-described fabric covering (if present) along the inflow rim, preferably at the mid-cusp point of each leaflet 20, to aid the surgeon in aligning the bioprosthesis 10 with the patient's natural aorta. For instance, if the cloth is white, the markings 32 may be stitches of navy blue thread, and the like. An exemplary light green marking thread is Polyester PTFE-Coated thread of 6.0 size, having a denier of 110–130.

Additional commissure markings 33 may also be formed on the fabric covering and/or inflow end of the bioprosthesis 10 at the locations of the valvular commissures to aid the surgeon in aligning the bioprosthesis with the patient's native anatomical structures. These optional commissure markings 33 may be formed in the same manner as described hereabove with respect to the mid-cusp markings 32, but will preferably of a color which is different from the mid-cusp markings 32 so as to permit the surgeon to easily distinguish between the mid-cusp markings 32 and commissure markings 33.

A valve retainer fixture may be attached to the outflow end OE of the bioprosthesis to facilitate the attachment of an elongate handle thereto. Such valve retainer fixture may be of the type described in U.S. Pat. No. 5,336,258 (Quintero et al.). Alternatively, in lieu of the use of such valve retainer fixture, the bioprosthesis may be mounted within a cage-like holding apparatus of the type described in U.S. Pat. No. 5,800,531, entitled Bioprosthetic Heart Valve Implantation Device.

The invention has been described hereabove with reference to certain presently preferred embodiments only, and no attempt has been made to exhaustively describe all possible embodiments of the invention. Indeed, those skilled in the art will recognize that various modifications, additions, deletions or alterations may be made to the above-described preferred embodiment without necessarily departing from the intended spirit and scope of the invention, and it is intended that such modifications, additions, deletions and alterations be included within the scope of the following claims.

What is claimed is:

1. A method of tanning an animal aortic bioprosthesis which comprises a segment of mammalian aorta having i) an aortic lumen extending longitudinally therethrough, ii) an inflow end, iii) an outflow end, iv) a plurality of aortic valve leaflets disposed within the aortic lumen; v) right and left coronary Sinuses of Valsalva, vi) a noncoronary sinus which is situated radially adjacent to and between the Sinuses of Valsalva, and vii) right and left coronary artery segments having coronary artery segment lumens extending therethrough, said coronary artery segments extending outwardly from the bioprosthesis, said method comprising the steps of:

(A) providing a support insert which comprises a substantially rigid tubular body having i) a bottom end, ii) a top end, iii) a hollow bore extending longitudinally therethrough, iv) right and left coronary Sinus of Valsalva support members extending upwardly at the top end of the tubular body at spaced apart locations and having generally convex outer surfaces, and v) a noncoronary Sinus of Valsalva support member extending upwardly at the top end of the tubular body and having a generally convex outer surface;

(B) placing the aortic bioprosthesis upon the support insert such that i) the coronary Sinus of Valsalva support members are positioned within the right and left coronary Sinuses of Valsalva, ii) the noncoronary Sinus of Valsalva support member is positioned within the noncoronary Sinus of Valsalva, and iii) the tubular body of the support insert extends through the aortic lumen of the bioprosthesis with the bottom end of the tubular body being located adjacent the outflow end of the bioprosthesis;

(C) subjecting the bioprosthesis, while positioned on the insert, to a tanning agent, to effect tanning of the bioprosthesis, and during the tanning step providing coronary artery segment lumen supports for maintaining the patency of the coronary artery segment lumens and causing said coronary artery segment lumen supports to maintain the patency of the coronary artery segment lumens;

(D) removing said coronary artery segment lumen supports after the step of tanning; and, (E) removing the bioprosthesis from the support insert.

2. The method of claim 1 wherein the coronary artery supports comprise mandrel members which are insertable into the coronary artery segment lumens to maintain the patency of the coronary artery segment lumens, and wherein the "causing" step comprises:

inserting said mandrel members into said coronary artery segment lumens; and the "removing" step comprises:

extracting the mandrel members from the coronary artery segment lumens after step C.

3. The method of claim 2 wherein the "causing" step further comprises:

placing a mandrel retaining apparatus upon said coronary artery segments to hold said mandrel members within the coronary artery segment lumens; and wherein the "removing" step comprises removing the mandrel retaining apparatus extracting the mandrel members from the coronary artery segment lumens, after step C.

4. The method of claim 3 wherein the mandrel retaining apparatus placed during the "causing" step are selected from the group of mandrel retaining apparatus consisting of:

a. ligatures placed about said coronary artery segments; and, b. clamps placed upon said coronary artery segments.

5. The method of claim 2 wherein said mandrel members have hollow bores extending longitudinally therethrough, and wherein the method further comprises the steps of:

providing pin members which are insertable through the hollow bores of the mandrel members and into a portion of said support insert;

inserting said pin members through the hollow bores of the mandrel members and into said support insert upon which said bioprosthesis is mounted, prior to the performance of step C, to thereby deter inadvertent longitudinal movement of the bioprosthesis on the support member during step C;

removing the pin members and mandrel members after step C.

6. The method claim 1 wherein step C comprises:

immersing the bioprosthesis mounted on the support insert in a tanning solution and maintaining a differential pressure of 0–4 mm Hg across the valve leaflets, the gradient of any such differential pressure being in a direction to urge the valve leaflets to a closed configuration.

7. An aortic bioprosthesis which comprises a segment of mammalian aorta having i) an aortic lumen extending longitudinally therethrough, ii) an inflow end, iii) an outflow end, iv) a plurality of aortic valve leaflets disposed within the aortic lumen; v) right and left coronary Sinuses of Valsalva, vi) a noncoronary sinus which is situated radially adjacent to and between the Sinuses of Valsalva, and vii) right and left coronary artery segments having coronary artery segment lumens extending therethrough, said coronary artery segments extending outwardly from the bioprosthesis, said bioprosthesis having been manufactured by a method comprising the steps of:

(A) providing a support insert which comprises a substantially rigid tubular body having i) a bottom end, ii) a top end, iii) a hollow bore extending longitudinally therethrough, iv) right and left coronary Sinus of Valsalva support members extending upwardly at the top end of the tubular body at spaced apart locations and having generally convex outer surfaces, and v) a noncoronary Sinus of Valsalva support member extending upwardly at the top end of the tubular body and having a generally convex outer surface;

(B) placing the aortic bioprosthesis upon the support insert such that i) the coronary Sinus of Valsalva support members are positioned within the right and left coronary Sinuses of Valsalva, ii) the noncoronary Sinus of Valsalva support member is positioned within the noncoronary Sinus of Valsalva, and iii) the tubular body of the support insert extends through the aortic lumen of the bioprosthesis with the bottom end of the tubular body being located adjacent the outflow end of the bioprosthesis;

(C) subjecting the bioprosthesis, while positioned on the insert, to a tanning agent, to effect tanning of the bioprosthesis, and during the tanning step providing coronary artery segment lumen supports for maintaining the patency of the coronary artery segment lumens and causing said coronary artery segment lumen supports to maintain the patency of the coronary artery segment lumens;

(D)) removing said coronary artery segment lumen supports after the step of tanning; and, (E) removing the bioprosthesis from the support insert.

8. The bioprosthesis of claim 7 wherein the coronary artery supports comprise mandrel members which are insertable into the coronary artery segment lumens to maintain the patency of the coronary artery segment lumens, and wherein the "causing" step of the method by which the bioprosthesis is manufactured comprises:

inserting said mandrel members into said coronary artery segment lumens; and wherein the "removing" step comprises:

extracting the mandrel members from the coronary artery segment lumens after step C.

9. The bioprosthesis of claim 8 wherein the "causing" step of the method by which the bioprosthesis is manufactured further comprises:

placing a mandrel retaining apparatus upon said coronary artery segments to hold said mandrel members within the coronary artery segment lumens;

and wherein the "removing" step comprises removing the mandrel retaining apparatus extracting the mandrel members from the coronary artery segment lumens, after step C.

10. The bioprosthesis of claim 9 wherein the mandrel retaining apparatus placed during the "causing" step of the method by which the bioprosthesis is manufactured are selected from the group of mandrel retaining apparatus consisting of:

a. ligatures placed about said coronary artery segments; and b. clamps placed upon said coronary artery segments.

11. The bioprosthesis of claim 8 wherein said mandrel members placed during the method by which the bioprosthesis is manufactured have hollow bores extending longitudinally therethrough, and wherein the method by which the bioprosthesis is manufactured further comprises the steps of:

providing pin members which are insertable through the hollow bores of the mandrel members and into a portion of said support insert;

inserting said pin members through the hollow bores of the mandrel members and into said support insert upon which said bioprosthesis is mounted, prior to the performance of step C, to thereby deter inadvertent longitudinal movement of the bioprosthesis on the support member during step C;

removing the pin members and mandrel members after step C.

12. The bioprosthesis of claim 7 wherein step C of the method by which the bioprosthesis is manufactured comprises:

immersing the bioprosthesis mounted on the support insert in a tanning solution and maintaining a differential pressure of 0–4 mm Hg across the valve leaflets, the gradient of any such differential pressure being in a direction to urge the valve leaflets to a closed configuration.

13. A method of tanning an animal aortic bioprosthesis which comprises a segment of mammalian aorta having:

an aortic lumen extending longitudinally therethrough, an inflow end, an outflow end, a plurality of aortic valve leaflets disposed within the aortic lumen, right and left coronary Sinuses of Valsalva, a noncoronary sinus which is situated radially adjacent to and between the Sinuses of Valsalva, and right and left coronary artery segments having coronary artery segment lumens extending therethrough, said coronary artery segments extending outwardly from the Sinuses of Valsalva, said method comprising the steps of:

providing a valve insert which comprises a substantially rigid tubular body;

placing the aortic bioprosthesis upon the valve insert;

internally supporting the right and left coronary artery segments with coronary supports extending outward and removably secured to the bioprosthesis;

subjecting the bioprosthesis, while positioned on the insert and with the coronary supports positioned within the coronary artery segments, to a tanning agent, to effect tanning of the bioprosthesis; and, removing the bioprosthesis from the valve insert.

14. The method of claim 13 wherein the coronary supports comprise mandrel members which are insertable into the coronary artery segment lumens to maintain the patency of the coronary artery segment lumens, and wherein the "internally supporting" step comprises inserting said mandrel members into said coronary artery segment lumens, and the "removing" step comprises extracting the mandrel members from the coronary artery segment lumens after the step of subjecting the bioprosthesis to a tanning agent.

15. The method of claim 14 wherein the mandrel members are formed of silicone tubing.

16. The method of claim 14 wherein the mandrel members are formed from a group consisting of:

polyurethane;

polytetrafluoroethylene;

polyethylene;

stainless steel;

titanium; and a metal alloy.

17. The method of claim 14 wherein the "internally supporting" step further comprises placing a mandrel retaining apparatus upon said coronary artery segments to hold said mandrel members within the coronary artery segment lumens, and wherein the "removing" step comprises removing the mandrel retaining apparatus extracting the mandrel members from the coronary artery segment lumens, after the step of subjecting the bioprosthesis to a tanning agent.

18. The method of claim 17 wherein the mandrel retaining apparatus placed during the "internally supporting" step are selected from the group of mandrel retaining apparatus consisting of:

ligatures placed about said coronary artery segments; and, clamps placed upon said coronary artery segments.

19. The method of claim 13 wherein said coronary supports have hollow bores extending longitudinally therethrough, the body having a plurality of holes formed therein, and wherein the method further comprises the steps of:

providing pin members which are insertable through the hollow bores of the coronary supports and into one of the holes of said valve insert;

inserting said pin members through the hollow bores of the coronary supports and into the holes of said valve insert prior to the step of subjecting the bioprosthesis to a tanning agent; and removing the pin members and coronary supports after the step of subjecting the bioprosthesis to a tanning agent.

20. The method claim 13 wherein the substantially rigid tubular body comprises:

a bottom end, a top end, a hollow bore extending longitudinally therethrough, right and left coronary sinus supports extending upwardly at the top end of the tubular body at spaced apart locations and having generally convex outer surfaces, the coronary sinus supports having a plurality of holes formed therein;

and wherein the method further includes:

positioning the right and left coronary Sinuses of Valsalva adjacent the holes formed in the body; and removably securing each of the coronary supports in one of the holes.

21. The method of claim 20 wherein said coronary supports are generally cylindrical and have hollow bores extending longitudinally therethrough, and the method further comprises the steps of:

providing pins which are insertable through the hollow bores of the coronary supports and into one of the holes of said valve insert;

inserting said pin members through the hollow bores of the coronary supports and into the holes of said valve insert prior to the step of subjecting the bioprosthesis to a tanning agent; and removing the pin members and coronary supports after the step of subjecting the bioprosthesis to a tanning agent.

22. The method of claim 20 wherein the coronary sinus supports have convex outer surfaces to conform to a dilated configuration of the coronary Sinuses of Valsalva of the bioprosthesis, the valve insert further including a noncoronary sinus support spaced from and sized smaller than the coronary supports and adapted to contact the noncoronary sinus.

* * * * *